United States Patent
Moran et al.

(12) 
(10) Patent No.: US 6,747,043 B2
(45) Date of Patent: Jun. 8, 2004

(54) ALKOXY ARYL $\beta_2$ ADRENERGIC RECEPTOR AGONISTS

(75) Inventors: Edmund J. Moran, San Francisco, CA (US); Eric Fournier, Laval (CA)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 10/445,643

(22) Filed: May 27, 2003

(65) Prior Publication Data

US 2004/0006102 A1 Jan. 8, 2004

Related U.S. Application Data

(60) Provisional application No. 60/383,747, filed on May 28, 2002.

(51) Int. Cl.⁷ .................. C07D 213/02; A61K 31/47; C07C 233/43
(52) U.S. Cl. .................. 514/312; 514/613; 514/646; 546/157; 564/123; 564/305
(58) Field of Search .................. 546/157; 564/123.305; 514/312, 613, 646

(56) References Cited

U.S. PATENT DOCUMENTS

| | | |
|---|---|---|
| 3,875,233 A | 4/1975 | Bastian et al. |
| 4,021,485 A | 5/1977 | Schromm et al. |
| 4,894,219 A | 1/1990 | Baker et al. |
| 4,992,474 A | 2/1991 | Skidmore et al. |
| 5,750,701 A | 5/1998 | Beeley et al. |
| 6,268,533 B1 | 7/2001 | Gao et al. |
| 6,436,914 B1 | 8/2002 | Sher et al. |
| 6,541,669 B1 | 4/2003 | Moran et al. |
| 6,576,793 B1 | 6/2003 | Moran et al. |

FOREIGN PATENT DOCUMENTS

| | | | |
|---|---|---|---|
| BE | 849 794 | 4/1977 | |
| CH | 550 768 | 2/1972 | |
| EP | 0 070 134 B1 | 11/1985 | |
| EP | 0 196 849 | 10/1986 | |
| EP | 0 233 686 | 8/1987 | |
| EP | 0 147 719 | 7/1989 | |
| FR | 2 147 188 | 3/1973 | |
| GB | 1040724 | 9/1966 | |
| JP | 10-152460 | 6/1998 | |
| WO | WO 01/42193 A1 * | 12/2000 | ......... C07C/233/43 |
| WO | WO 02/066422 A1 | 8/2002 | |
| WO | WO 02/070490 A1 | 9/2002 | |
| WO | WO 02/076933 A1 | 10/2002 | |
| WO | WO 03/024439 A1 | 3/2003 | |

OTHER PUBLICATIONS

Johnson, Malcolm, "Salmeterol", Medicinal Research Reviews, vol. 15, No. 3, pp 225–257 (1995).

Uehling et al., "Synthesis and Evaluation of Potent and Selective $\beta_3$ Adrenergic Receptor Agonists Containing Acylsulfonamide, Sulfonylsulfonamide, and Sulfonylurea Carboxylic Acid Isosteres", J. Med. Chem., vol. 45, pp 567–583 (2002).

Yokoi et al., "The Development of a Radioimmunoassay for Formoterol", Life Sciences, vol. 33, pp 1665–1672 (1983).

\* cited by examiner

*Primary Examiner*—Zinna Northington Davis
(74) *Attorney, Agent, or Firm*—Robert P. Saxon; Jeffrey A. Hagenah

(57) ABSTRACT

The invention provides novel $\beta_2$ adrenergic receptor agonist compounds. The invention also provides pharmaceutical compositions comprising such compounds, methods of using such compounds to treat diseases associated with $\beta_2$ adrenergic receptor activity, and processes and intermediates useful for preparing such compounds.

30 Claims, No Drawings

ALKOXY ARYL β₂ ADRENERGIC RECEPTOR AGONISTS

CROSS REFERENCE TO RELATED APPLICATION

This application claims the benefit of U.S. Provisional Application No. 60/383,747, filed May 28, 2002, the disclosure of which is incorporated herein by reference.

FIELD OF THE INVENTION

The invention is directed to novel $\beta_2$ adrenergic receptor agonists. The invention is also directed to pharmaceutical compositions comprising such compounds, methods of using such compounds to treat diseases associated with $\beta_2$ adrenergic receptor activity, and processes and intermediates useful for preparing such compounds.

BACKGROUND OF THE INVENTION $\beta_2$ adrenergic receptor agonists are recognized as effective drugs for the treatment of pulmonary diseases such as asthma and chronic obstructive pulmonary disease (including chronic bronchitis and emphysema). $\beta_2$ adrenergic receptor agonists are also useful for treating pre-term labor, and are potentially useful for treating neurological disorders and cardiac disorders. In spite of the success that has been achieved with certain $\beta_2$ adrenergic receptor agonists, current agents possess less than desirable potency, selectivity, onset, and/or duration of action. Thus, there is a need for additional $\beta_2$ adrenergic receptor agonists having improved properties. Preferred agents may possess, among other properties, improved potency, selectivity, onset, and/or duration of action.

SUMMARY OF THE INVENTION

The invention provides novel compounds that possess $\beta_2$ adrenergic receptor agonist activity. Accordingly, there is provided a compound of the invention which is a compound of formula (I):

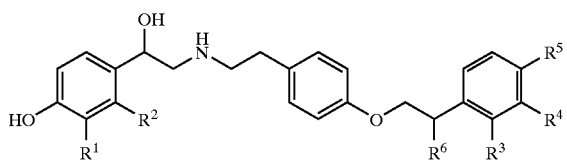

(I)

wherein:
$R^1$ is —CH$_2$OH or —NHCHO, and $R^2$ is hydrogen; or $R^1$ and $R^2$ taken together are —NHC(=O)CH=CH—;
$R^3$, $R^4$, and $R^5$ are each independently hydrogen, halo, alkyl, alkoxy, or aryl, wherein each alkyl and alkoxy is optionally substituted with one or more halo; or $R^3$ and $R^4$ together form a fused benzo ring; or $R^4$ and $R^5$ together form a fused benzo ring; and
$R^6$ is hydrogen or hydroxy;
or a pharmaceutically-acceptable salt or solvate or stereoisomer thereof.

The invention also provides a pharmaceutical composition comprising a compound of the invention and a pharmaceutically-acceptable carrier. The invention further provides combinations comprising a compound of the invention and one or more other therapeutic agents and pharmaceutical compositions comprising such combinations.

The invention also provides a method of treating a disease or condition associated with $\beta_2$ adrenergic receptor activity (e.g. a pulmonary disease, such as asthma or chronic obstructive pulmonary disease, pre-term labor, a neurological disorder, a cardiac disorder, or inflammation) in a mammal, comprising administering to the mammal, a therapeutically effective amount of a compound of the invention. The invention further provides a method of treatment comprising administering a therapeutically effective amount of a combination of a compound of the invention together with one or more other therapeutic agents.

The invention also provides a method of treating a disease or condition associated with $\beta_2$ adrenergic receptor activity (e.g. a pulmonary disease, such as asthma or chronic obstructive pulmonary disease, pre-term labor, a neurological disorder, a cardiac disorder, or inflammation) in a mammal, comprising administering to the mammal, a therapeutically effective amount of a pharmaceutical composition of the invention.

This invention also provides a method of modulating a $\beta_2$ adrenergic receptor, the method comprising stimulating a $\beta_2$ adrenergic receptor with a modulatory amount of a compound of the invention.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with $\beta_2$ adrenergic receptor activity (e.g. a pulmonary disease, such as asthma or chronic obstructive pulmonary disease, pre-term labor, a neurological disorder, a cardiac disorder, or inflammation) in a mammal.

DETAILED DESCRIPTION OF THE INVENTION

When describing the compounds, compositions and methods of the invention, the following terms have the following meanings, unless otherwise indicated.

The term "alkyl" refers to a monovalent saturated hydrocarbon group which may be linear or branched or combinations thereof. Such alkyl groups preferably contain from 1 to 20 carbon atoms; more preferably, from 1 to 8 carbon atoms; and still more preferably, from 1 to 4 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkoxy" refers to a group of the formula —OR, where R is an alkyl group as defined herein. Representative alkoxy groups include, by way of example, methoxy, ethoxy, n-propoxy, isopropoxy, n-butoxy, sec-butoxy, isobutoxy, tert-butoxy, n-pentoxy, n-hexoxy and the like.

The term "aryl" refers to a monovalent carbocyclic group which may be monocyclic or multicyclic (i.e., fused) wherein at least one ring is aromatic. Such aryl groups preferably contain from 6 to 20 carbon atoms, more preferably, from 6 to 10 carbon atoms. This term includes multicyclic carbocyclic ring systems wherein one or more rings are not aromatic, provided the point of attachment is on an aromatic ring. Representative aryl groups include, by way of example, phenyl, napthyl, azulenyl, indan-5-yl, 1,2,3,4-tetrahydronaphth-6-yl, and the like.

The term "halo" refers to a fluoro, chloro, bromo or iodo.

The term "therapeutically effective amount" refers to an amount sufficient to effect treatment when administered to a patient in need of treatment.

The term "treatment" as used herein refers to the treatment of a disease or medical condition in a patient, such as a mammal (particularly a human) which includes:

(a) preventing the disease or medical condition from occurring, i.e., prophylactic treatment of a patient;

(b) ameliorating the disease or medical condition, i.e., eliminating or causing regression of the disease or medical condition in a patient;

(c) suppressing the disease or medical condition, i.e., slowing or arresting the development of the disease or medical condition in a patient; or (d) alleviating the symptoms of the disease or medical condition in a patient.

The phrase "disease or condition associated with $\beta_2$ adrenergic receptor activity" includes all disease states and/or conditions that are acknowledged now, or that are found in the future, to be associated with $\beta_2$ adrenergic receptor activity. Such disease states include, but are not limited to, pulmonary diseases, such as asthma and chronic obstructive pulmonary disease (including chronic bronchitis and emphysema), as well as neurological disorders and cardiac disorders. $\beta_2$ adrenergic receptor activity is also known to be associated with pre-term labor (see U.S. Pat. No. 5,872,126) and some types of inflammation (see International Patent Application Publication Number WO 99/30703 and U.S. Pat. No. 5,290,815).

The term "pharmaceutically-acceptable salt" refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

Salts derived from pharmaceutically-acceptable acids include acetic, benzenesulfonic, benzoic, camphosulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid) and the like. Particularly preferred are salts derived from fumaric, hydrobromic, hydrochloric, acetic, sulfuric, methanesulfonic, xinafoic, and tartaric acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like.

The term "solvate" refers to a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate of stereoisomer thereof" is intended to include all permutations of salts, solvates and stereoisomers, such as a solvate of a pharmaceutically-acceptable salt of a stereoisomer of a compound of formula (I).

The term "leaving group" refers to a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" refers to a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" refers to a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Specific and preferred values listed below for radicals, substituents, and ranges, are for illustration only; they do not exclude other defined values or other values within defined ranges for the radicals and substituents.

A specific value for $R^3$ is hydrogen, alkoxy or halo.

Another specific value for $R^3$ is hydrogen, methoxy, or fluoro.

A specific value for $R^4$ is hydrogen, alkoxy or halo.

Another specific value for $R^4$ is hydrogen, methoxy, or fluoro.

A specific value for $R^4$ and $R^5$ together is a fused benzo ring.

A specific value for $R^5$ is hydrogen, alkyl, aryl, alkoxy or halo.

Another specific value for $R^5$ is hydrogen, fluoro, chloro, methoxy, trifluoromethoxy, difluoromethoxy, 3-methylbutyl, or phenyl.

A preferred group of compounds of formula (I) are compounds wherein $R^3$ is hydrogen or methoxy; $R^4$ is hydrogen or methoxy; and $R^5$ is hydrogen.

Another preferred group of compounds of formula (I) are compounds wherein $R^3$ is hydrogen; $R^4$ is hydrogen; and $R^5$ is hydrogen.

Another preferred group of compounds of formula (I) are compounds wherein $R^3$ is hydrogen; $R^4$ is hydrogen; and $R^5$ is fluoro.

A specific value for $R^6$ is hydroxy.
A specific value for $R^6$ is hydrogen.
One preferred compound of formula (I) is a compound of formula (II):

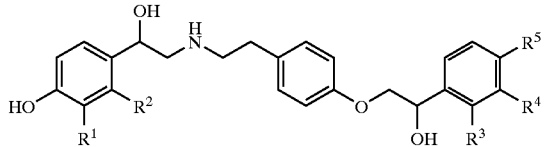

(II)

wherein:
$R^1$ is —$CH_2OH$ or —NHCHO, and $R^2$ is hydrogen; or $R^1$ and $R^2$ taken together are —NHC(=O)CH=CH—; and
$R^3$, $R^4$, and $R^5$ are each independently hydrogen, halo, alkyl, alkoxy, or aryl, wherein each alkyl and alkoxy is optionally substituted with one or more halo; or $R^3$ and $R^4$ together form a fused benzo ring; or $R^4$ and $R^5$ together form a fused benzo ring; or a pharmaceutically-acceptable salt or solvate or stereoisomer thereof.

A preferred group of compounds of formula (II) are compounds wherein $R^3$ is hydrogen or methoxy; $R^4$ is hydrogen or methoxy; and $R^5$ is hydrogen.

Another preferred group of compounds of formula (II) are compounds wherein $R^3$ is hydrogen; $R^4$ is hydrogen; and $R^5$ is hydrogen.

Another preferred group of compounds of formula (II) are compounds wherein $R^3$ is hydrogen; $R^4$ is hydrogen; and $R^5$ is fluoro.

Another preferred compound of formula (I) is a compound of formula (III):

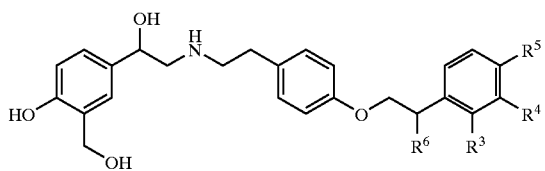

(III)

wherein: $R^3$, $R^4$, and $R^5$ are each independently hydrogen, halo, alkyl, alkoxy, or aryl, wherein each alkyl and alkoxy is optionally substituted with one or more halo; or $R^3$ and $R^4$ together form a fused benzo ring; or $R^4$ and $R^5$ together form a fused benzo ring; and $R^6$ is hydrogen or hydroxy; or a pharmaceutically-acceptable salt or solvate or stereoisomer thereof.

Another preferred compound of formula (I) is a compound of formula (IV):

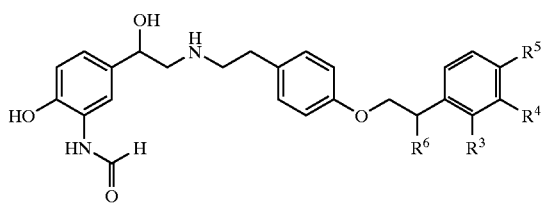

(IV)

wherein: $R^3$, $R^4$, and $R^5$ are each independently hydrogen, halo, alkyl, alkoxy, or aryl, wherein each alkyl and alkoxy is optionally substituted with one or more halo; or $R^3$ and $R^4$ together form a fused benzo ring; or $R^4$ and $R^5$ together form a fused benzo ring; and $R^6$ is hydrogen or hydroxy; or a pharmaceutically-acceptable salt or solvate or stereoisomer thereof.

Another preferred compound of formula (I) is a compound of formula (V):

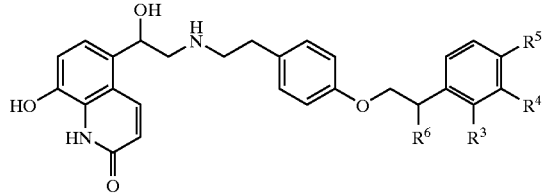

(V)

wherein: $R^3$, $R^4$, and $R^5$ are each independently hydrogen, halo, alkyl, alkoxy, or aryl, wherein each alkyl and alkoxy is optionally substituted with one or more halo; or $R^3$ and $R^4$ together form a fused benzo ring; or $R^4$ and $R^5$ together form a fused benzo ring; and $R^6$ is hydrogen or hydroxy; or a pharmaceutically-acceptable salt or solvate or stereoisomer thereof.

Exemplary compounds of the invention are compounds 1–25 as described in the Examples below. Preferred compounds of the invention are compounds 1–6, 8–11, 14–16, and 18–25. A more preferred sub-group of compounds is compounds 1, 2, 4–6, 19, 20, 22–25.

Particular mention may be made of the following compounds for which the compound numbers are indicated in parentheses:
4-((R)-1-Hydroxy-2-{2-[4-((R)-2-hydroxy-2-phenyl-ethoxy)-phenyl]-ethylamino}-ethyl)-2-hydroxymethyl-phenol (20);
4-[(R)-1-Hydroxy-2-(2-{4-[(R)-2-hydroxy-2-(2-methoxy-phenyl)-ethoxy]-phenyl}-ethylamino)-ethyl]-2-hydroxymethyl-phenol (21);
N-[2-Hydroxy-5-((R)-1-hydroxy-2-{2-[4-((R)-2-hydroxy-2-phenyl-ethoxy)-phenyl]-ethylamino}-ethyl)-phenyl]-formamide (22);
N-{2-Hydroxy-5-[(R)-1-hydroxy-2-(2-{4-[(R)-2-hydroxy-2-(2-methoxy-phenyl)-ethoxy]-ethylamino}ehtyl]-phenyl}-formamide (23);
8-Hydroxy-5-((R)-1-hydroxy-2-{2-[4-((R)-2-hydroxy-2-phenyl-ethoxy)-phenyl]-ethylamino}-ethyl)-1H-quinolin-2-one (24); and
8-Hydroxy-5-[(R)-1-hydroxy-2-(2-{4-[(R)-2-hydroxy-2-(2-methoxy-phenyl)-ethoxy]-phenyl}-ethylamino)-ethyl]-1H-quinolin-2-one (25). (25).

The compounds of the invention may contain a chiral center. Accordingly, the invention includes racemic mixtures, enantiomers, and mixtures enriched in one or more stereoisomer. The scope of the invention as described and claimed encompasses the racemic forms of the compounds as well as the individual enantiomers, diastereomers, and stereoisomer-enriched mixtures. A preferred compound of the invention is a compound that is a mixture of enantiomers, wherein the amount of the (R) enantiomer at the chiral center in formula (I) or formula (II) that is attached to the phenyl ring substituted with $R^1$ and $R^2$ is greater than the amount of the (S) enantiomer. A more preferred compound of the invention is a compound that is the (R) enantiomer at this center.

When $R^6$ is hydroxy, or, equivalently, when the compound is a compound of formula (II), another preferred compound of the invention is a compound that is a mixture of enantiomers, wherein the amount of the (R) enantiomer at the chiral center attached to the phenyl ring substituted with $R^3$, $R^4$, and $R^5$ (i.e. in formula (I), the chiral center substituted with $R^6$) is greater than the amount of the (S) enantiomer at this center. A more preferred compound of the invention is a compound that is the (R) enantiomer at this center.

Further, when $R^6$ is hydroxy, or the compound is a compound of formula (II), a preferred diastereomer of the invention is a compound that is a mixture of diastereomers, wherein the amount of the (R, R) diastereomer at the two chiral centers identified above in formula (I) or (II) is greater than the amount of other diastereomers. A more preferred compound of the invention when $R^6$ is hydroxy, or when the compound is a compound of formula (II), is a compound that is the (R, R) diastereomer at the two chiral centers of formula (I) or formula (II).

General Synthetic Procedures

The compounds of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis,* Third Edition, Wiley, New York, 1999, and references cited therein.

Processes for preparing compounds of the invention are provided as further embodiments of the invention and are illustrated by the procedures below.

For example, a compound of formula (I) can be prepared from a corresponding intermediate compound of formula (VI):

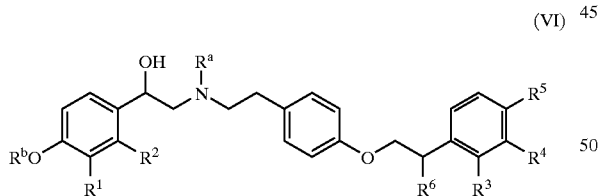

(VI)

wherein $R^a$ is a amino-protecting group (e.g. benzyl) and $R^b$ is hydrogen, by removing the protecting group $R^a$ to provide the compound of formula (I).

A compound of formula (I) can also be prepared from a corresponding intermediate compound of formula (VI) wherein $R^a$ is hydrogen and $R^b$ is a hydroxy-protecting group (e.g. benzyl), by removing the protecting group $R^b$ to provide the compound of formula (I).

A compound of formula (I) can also be prepared from a corresponding intermediate compound of formula (VI) wherein $R^a$ is a amino-protecting group (e.g. benzyl) and $R^b$ is a hydroxy-protecting group (e.g. benzyl), by removing the protecting groups ($R^a$ and $R^b$) to provide the compound of formula (I).

An intermediate compound of formula (VI) can be prepared by alkylating a corresponding alcohol of formula (VII) with a corresponding compound of formula (VIII), wherein Z is a suitable leaving group (e.g. bromo, iodo, tosyl, or mesyl).

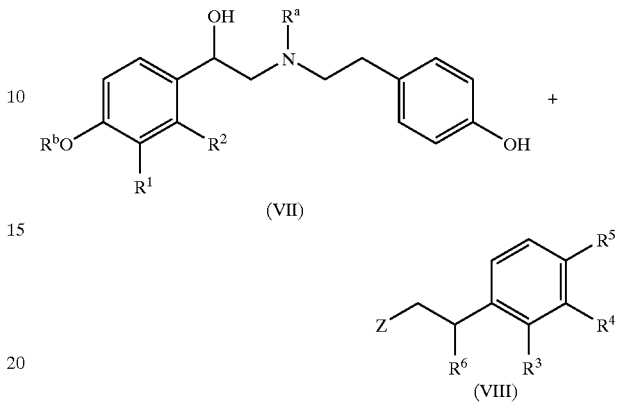

Suitable conditions for such alkylations are well known, and are illustrated in the Examples hereinbelow.

Accordingly, the invention provides a method for preparing a compound of formula (VI):

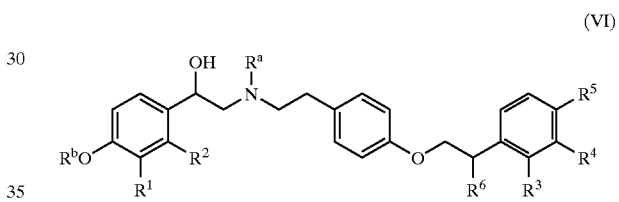

(VI)

wherein $R^a$ is a amino-protecting group (e.g. benzyl); $R^b$ is a hydroxy-protecting group (e.g. benzyl); and $R^1$–$R^6$ have any of the values, specific values or preferred values described herein, comprising alkylating a corresponding alcohol of formula (VII) with a corresponding compound of formula (VIII):

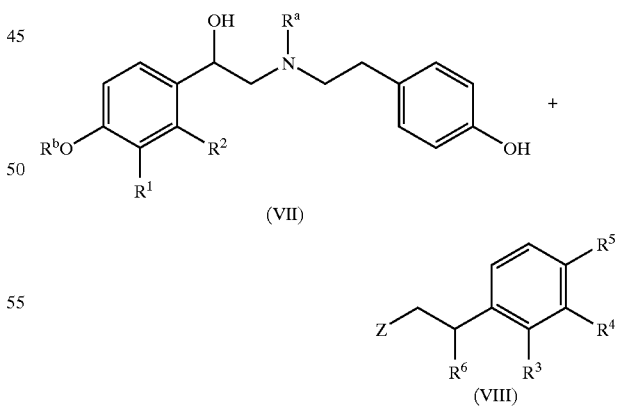

wherein Z is a suitable leaving group (e.g. bromo, iodo, tosyl, or mesyl), to provide the compound of formula (VI).

The invention also provides novel compounds of formulae (VI–VIII) described herein.

Pharmaceutical Compositions

The invention also provides pharmaceutical compositions comprising a compound of the invention. Accordingly, the compound, preferably in the form of a pharmaceutically-acceptable salt, can be formulated for any suitable form of administration, such as oral or parenteral administration, or administration by inhalation.

By way of illustration, the compound can be admixed with conventional pharmaceutical carriers and excipients and used in the form of powders, tablets, capsules, elixirs, suspensions, syrups, wafers, and the like. Such pharmaceutical compositions will contain from about 0.05 to about 90% by weight of the active compound, and more generally from about 0.1 to about 30%. The pharmaceutical compositions may contain common carriers and excipients, such as cornstarch or gelatin, lactose, magnesium sulfate, magnesium stearate, sucrose, microcrystalline cellulose, kaolin, mannitol, dicalcium phosphate, sodium chloride, and alginic acid. Disintegrators commonly used in the formulations of this invention include croscarmellose, microcrystalline cellulose, cornstarch, sodium starch glycolate and alginic acid.

A liquid composition will generally consist of a suspension or solution of the compound or pharmaceutically-acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, polyvinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically-acceptable salts that are active when given parenterally can be formulated for intramuscular, intrathecal, or intravenous administration.

A typical composition for intra-muscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetraacetic acid; a solubilizing agent, for example, a cyclodextrin; and an anti-oxidant, for example, sodium metabisulphite, may be included in the formulation. Alternatively, the solution can be freeze dried and then reconstituted with a suitable solvent just prior to administration.

The compounds of this invention and their pharmaceutically-acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252. Such patches may be constructed for continuous, pulsatile, or on demand delivery of pharmaceutical agents.

One preferred manner for administering a compound of the invention is inhalation. Inhalation is an effective means for delivering an agent directly to the respiratory tract. There are three general types of pharmaceutical inhalation devices: nebulizer inhalers, dry powder inhalers (DPI), and metered-dose inhalers (MDI). Nebulizer devices produce a stream of high velocity air that causes a therapeutic agent to spray as a mist which is carried into the patient's respiratory tract. The therapeutic agent is formulated in a liquid form such as a solution or a suspension of micronized particles of respirable size, where micronized is typically defined as having about 90% or more of the particles with a diameter of less than about 10 $\mu$m. A typical formulation for use in a conventional nebulizer device is an isotonic aqueous solution of a pharmaceutical salt of the active agent at a concentration of the active agent of between about 0.05 $\mu$g/mL and about 10 mg/mL.

DPI's typically administer a therapeutic agent in the form of a free flowing powder that can be dispersed in a patient's air-stream during inspiration. In order to achieve a free flowing powder, the therapeutic agent can be formulated with a suitable excipient, such as lactose or starch. A dry powder formulation can be made, for example, by combining dry lactose having a particle size between about 1 $\mu$m and about 100 $\mu$m with micronized particles of a pharmaceutical salt of the active agent and dry blending. Alternative, the agent can be formulated without excipients. The formulation is loaded into a dry powder dispenser, or into inhalation cartridges or capsules for use with a dry powder delivery device.

Examples of DPI delivery devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI's typically discharge a measured amount of therapeutic agent using compressed propellant gas. Formulations for MDI administration include a solution or suspension of active ingredient in a liquefied propellant. While chlorofluorocarbons, such as $CCl_3F$, conventionally have been used as propellants, due to concerns regarding adverse affects of such agents on the ozone layer, formulations using hydrofluoroalklanes (HFA), such as 1,1,1,2-tetrafluoroethane (HFA 134a) and 1,1,1,2,3,3,3,-heptafluoro-n-propane, (HFA 227) have been developed. Additional components of HFA formulations for MDI administration include co-solvents, such as ethanol or pentane, and surfactants, such as sorbitan trioleate, oleic acid, lecithin, and glycerin. (See, for example, U.S. Pat. No. 5,225,183, EP 0717987 A2, and WO 92/22286.)

Thus, a suitable formulation for MDI administration can include from about 0.01% to about 5% by weight of a pharmaceutical salt of active ingredient, from about 0% to about 20% by weight ethanol, and from about 0% to about 5% by weight surfactant, with the remainder being the HFA propellant. In one approach, to prepare the formulation, chilled or pressurized hydrofluoroalkane is added to a vial containing the pharmaceutical salt of active compound, ethanol (if present) and the surfactant (if present). To prepare a suspension, the pharmaceutical salt is provided as micronized particles. The formulation is loaded into an aerosol canister, which forms a portion of an MDI device. Examples of MDI devices developed specifically for use with HFA propellants are provided in U.S. Pat. Nos. 6,006,745 and 6,143,277.

In an alternative preparation, a suspension formulation is prepared by spray drying a coating of surfactant on micronized particles of a pharmaceutical salt of active compound. (See, for example, WO 99/53901 and WO 00/61108.) For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

It will be understood that any form of the compounds of the invention, (i.e. free base, pharmaceutical salt, or solvate) that is suitable for the particular mode of administration, can be used in the pharmaceutical compositions discussed above.

The active compounds are effective over a wide dosage range and are generally administered in a therapeutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses of the therapeutic agents for inhalation administration are in the general range of from about 0.05 μg/day to about 1000 μg/day, preferably from about 0.5 μg/day to about 500 μg/day. A compound can be administered in a periodic dose: weekly, multiple times per week, daily, or multiple doses per day. The treatment regimen may require administration over extended periods of time, for example, for several weeks or months, or the treatment regimen may require chronic administration. Suitable doses for oral administration are in the general range of from about 0.05 μg/day to about 100 mg/day, preferably 0.5 to 1000 μg/day.

The present active agents can also be co-administered with one or more other therapeutic agents. For example, the present agents can be administered in combination with one or more therapeutic agents selected from anti-inflammatory agents (e.g. corticosteroids and non-steroidal anti-inflammatory agents (NSAIDs), antichlolinergic agents (particularly muscarinic receptor antagonists), other $\beta_2$ adrenergic receptor agonists, antiinfective agents (e.g. antibiotics or antivirals) or antihistamines. The invention thus provides, in a further aspect, a combination comprising a compound of the invention together with one or more therapeutic agent, for example, an anti-inflammatory agent, an antichlolinergic agent, another $\beta_2$ adrenergic receptor agonist, an antiinfective agent or an antihistamine.

The other therapeutic agents can be used in the form of pharmaceutically-acceptable salts or solvates. As appropriate, the other therapeutic agents can be used as optically pure stereoisomers.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid acid S-fluoromethyl ester.

Suitable NSAIDs include sodium cromoglycate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (αIL antibody), specifically, an αIL-4 therapy, an αIL-13 therapy, or a combination thereof); or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Also of interest is use of the present active agent in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl) cyclohexan-1-one and cis-[4-cyano-4-(3-cyclopropylmethoxy-4-difluoromethoxyphenyl) cyclohexan-1-ol].

Other compounds of interest include:

Compounds set out in U.S. Pat. No. 5,552,438 issued 03 Sep. 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms;

AWD-12-281 from elbion (Hofgen, N. et al. 15th EFMC Int Symp Med Chem (September 6–10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19–23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (-)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther,1998, 284(1): 162), and T2585.

Other possible PDE-4 and mixed PDE3/PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$, $M_2$, or $M_3$ receptors, or of combinations thereof. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, are characterized, based on their core structures, as ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic a tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlorpheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically-acceptable salt.

Azelastine hydrochloride is yet another $H_1$ receptor antagonist which may be used in combination with a compound of the invention.

Examples of preferred anti-histamines include methapyrilene and loratadine.

The invention thus provides, in a further aspect, a combination comprising a compound of formula (I) or a pharmaceutically-acceptable salt or solvate or stereoisomer thereof and a corticosteroid. In particular, the invention provides a combination wherein the corticosteroid is fluticasone propionate or wherein the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester or 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester.

The invention thus provides, in a further aspect, a combination comprising a compound of formula (I) or a pharmaceutically-acceptable salt or solvate or stereoisomer thereof and a PDE4 inhibitor.

The invention thus provides, in a further aspect, a combination comprising a compound of formula (I) or a pharmaceutically-acceptable salt or solvate or stereoisomer thereof and an anticholinergic agent.

The invention thus provides, in a further aspect, a combination comprising a compound of formula (I) or a pharmaceutically-acceptable salt or solvate or stereoisomer thereof and an antihistamine.

The invention thus provides, in a further aspect, a combination comprising a compound of formula (I) or a pharmaceutically-acceptable salt or solvate or stereoisomer thereof together with a PDE4 inhibitor and a corticosteroid.

The invention thus provides, in a further aspect, a combination comprising a compound of formula (I) or a pharmaceutically-acceptable salt or solvate or stereoisomer thereof together with an anticholinergic agent and a corticosteroid.

As used in the above combinations, the term, "a compound of formula (I)" includes a compound of formulas (II), (III), (IV), or (V), and preferred groups thereof, and any individually disclosed compound or compounds.

Accordingly, the pharmaceutical compositions of the invention can optionally comprise combinations of a compound of formula (I) or a pharmaceutically-acceptable salt or solvate or stereoisomer thereof with one or more other therapeutic agents, as described above.

The individual compounds of such combinations may be administered either sequentially or simultaneously in separate or combined pharmaceutical formulations. Appropriate doses of known therapeutic agents will be readily appreciated by those skilled in the art. Methods of treatment of the invention, therefore, include administration of the individual compounds of such combinations either sequentially or simultaneously in separate or combined pharmaceutical formulations.

Thus, according to a further aspect, the invention provides a method of treating a disease or condition associated with $\beta_2$ adrenergic receptor activity in a mammal, comprising administering to the mammal a therapeutically effective amount of a combination of a compound of formula (I) or a pharmaceutically-acceptable salt or solvate or stereoisomer thereof with one or more other therapeutic agents.

Additional suitable carriers for formulations of the active compounds of the present invention can be found in *Remington: The Science and Practice of Pharmacy, 20th Edition,* Lippincott Williams & Wilkins, Philadelphia, Pa., 2000. The following non-limiting examples illustrate representative pharmaceutical compositions of the invention.

Formulation Example A

This example illustrates the preparation of a representative pharmaceutical composition for oral administration of a compound of this invention:

| Ingredients | Quantity per tablet, (mg) |
| --- | --- |
| Active Compound | 1 |
| Lactose, spray-dried | 148 |
| Magnesium stearate | 2 |

The above ingredients are mixed and introduced into a hard-shell gelatin capsule.

Formulation Example B

This example illustrates the preparation of another representative pharmaceutical composition for oral administration of a compound of this invention:

| Ingredients | Quantity per tablet, (mg) |
| --- | --- |
| Active Compound | 1 |
| Cornstarch | 50 |
| Lactose | 145 |
| Magnesium stearate | 5 |

The above ingredients are mixed intimately and pressed into single scored tablets.

Formulation Example C

This example illustrates the preparation of a representative pharmaceutical composition for oral administration of a compound of this invention.

An oral suspension is prepared having the following composition.

| Ingredients | |
| --- | --- |
| Active Compound | 3 mg |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

Formulation Example D

This example illustrates the preparation of a representative pharmaceutical composition containing a compound of this invention.

An injectable preparation buffered to a pH of 4 is prepared having the following composition:

| Ingredients | |
| --- | --- |
| Active Compound | 0.1 mg |
| Sodium Acetate Buffer Solution (0.4 M) | 2.0 mL |
| HCl (1N) | q.s. to pH 4 |
| Water (distilled, sterile) | q.s. to 20 mL |

Formulation Example E

This example illustrates the preparation of a representative pharmaceutical composition for injection of a compound of this invention.

A reconstituted solution is prepared by adding 20 mL of sterile water to 1 mg of the compound of this invention. Before use, the solution is then diluted with 200 mL of an intravenous fluid that is compatible with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection.

Formulation Example F

This example illustrates the preparation of a representative pharmaceutical composition containing a compound of this invention.

An injectable preparation is prepared having the following composition:

| Ingredients | |
|---|---|
| Active Compound | 0.1–5.0 mg |
| Hydroxypropyl-β-cyclodextrin | 1–25 g |
| 5% Aqueous Dextrose Solution (sterile) | q.s. to 100 mL |

The above ingredients are blended and the pH is adjusted to 3.5±0.5 using 0.5 N HCl or 0.5 N NaOH.

Formulation Example G

This example illustrates the preparation of a representative pharmaceutical composition for topical application of a compound of this invention.

| Ingredients | grams |
|---|---|
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Formulation Example H

This example illustrates the preparation of a representative pharmaceutical composition containing a compound of the invention.

An aqueous aerosol formulation for use in a nebulizer is prepared by dissolving 0.1 mg of a pharmaceutical salt of active compound in a 0.9% sodium chloride solution acidified with citric acid. The mixture is stirred and sonicated until the active salt is dissolved. The pH of the solution is adjusted to a value in the range of from 3 to 8 by the slow addition of NaOH.

Formulation Example I

This example illustrates the preparation of a dry powder formulation containing a compound of the invention for use in inhalation cartridges.

Gelatin inhalation cartridges are filled with a pharmaceutical composition having the following ingredients:

| Ingredients | mg/cartridge |
|---|---|
| Pharmaceutical salt of active compound | 0.2 |
| Lactose | 25 |

The pharmaceutical salt of active compound is micronized prior to blending with lactose. The contents of the cartridges are administered using a powder inhaler.

Formulation Example J

This example illustrates the preparation of a dry powder formulation containing a compound of the invention for use in a dry powder inhalation device.

A pharmaceutical composition is prepared having a bulk formulation ratio of micronized pharmaceutical salt to lactose of 1:200. The composition is packed into a dry powder inhalation device capable of delivering between about 10 μg and about 100 μg of active drug ingredient per dose.

Formulation Example K

This example illustrates the preparation of a formulation containing a compound of the invention for use in a metered dose inhaler.

A suspension containing 5% pharmaceutical salt of active compound, 0.5% lecithin, and 0.5% trehalose is prepared by dispersing 5 g of active compound as micronized particles with mean size less than 10 μm in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

Formulation Example L

This example illustrates the preparation of a formulation containing a compound of the invention for use in a metered dose inhaler.

A suspension containing 5% pharmaceutical salt of active compound and 0.1% lecithin is prepared by dispersing 10 g of active compound as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into canisters with pressurized 1,1,1,2,3,3,3-heptafluoro-n-propane.

Biological Assays

The compounds of this invention, and their pharmaceutically-acceptable salts, exhibit biological activity and are useful for medical treatment. The ability of a compound to bind to the $\beta_2$ adrenergic receptor, as well as its selectivity, agonist potency, and intrinsic activity can be demonstrated using Tests A-B below, or can be demonstrated using other tests that are known in the art.

| Abbreviations | |
|---|---|
| % Eff | % efficacy |
| ATCC | American Type Culture Collection |
| BSA | Bovine Serum Albumin |
| cAMP | Adenosine 3′:5′-cyclic monophosphate |
| DMEM | Dulbecco's Modified Eagle's Medium |
| DMSO | Dimethyl sulfoxide |
| EDTA | Ethylenediaminetetraacetic acid |
| Emax | maximal efficacy |
| FBS | Fetal bovine serum |
| Gly | Glycine |
| HEK-293 | Human embryonic kidney-293 |
| PBS | Phosphate buffered saline |
| rpm | rotations per minute |
| Tris | Tris(hydroxymethyl)aminomethane |

Membrane Preparation From Cells Expressing Human $\beta_1$ or $\beta_2$ Adrenergic Receptors HEK-293 derived cell lines stably expressing cloned human $\beta_1$ or $\beta_2$ adrenergic receptors, respectively, were grown to near confluency in DMEM with 10% dialyzed FBS in the presence of 500 μg/mL Geneticin. The cell monolayer was lifted with Versene 1:5,000 (0.2 g/L EDTA in PBS) using a cell scraper. Cells were pelleted by centrifugation at 1,000 rpm, and cell pellets were either stored frozen at −80° C. or membranes were prepared immediately. For preparation, cell pellets were resuspended in lysis buffer (10 mM Tris/HCL pH 7.4 @ 4° C., one tablet of "Complete Protease Inhibitor Cocktail Tablets with 2 mM EDTA" per 50 mL buffer (Roche cat. #1697498, Roche Molecular Biochemicals, Indianapolis, Ind.)) and homogenized using a tight-fitting Dounce glass homogenizer (20 strokes) on ice. The homogenate was centrifuged at 20,000×g, the pellet was washed once with lysis buffer by resuspension and centrifugation as above. The final pellet was resuspended in membrane buffer (75 mM Tris/HCl pH 7.4, 12.5 mM $MgCl_2$, 1 mM EDTA @ 25° C.). Protein concentration of the membrane suspension was determined by the method of Bradford (Bradford M M., *Analytical Biochemistry*, 1976, 72, 248–54). Membranes were stored frozen in aliquots at −80° C.

Test A

Radioligand Binding Assay on Human $β_1$ and $β_2$ Adrenergic Receptors

Binding assays were performed in 96-well microtiter plates in a total assay volume of 100 μL with 5 μg membrane protein for membranes containing the human $β_2$ adrenergic receptor, or 2.5 μg membrane protein for membranes containing the human $β_1$ adrenergic receptor in assay buffer (75 mM Tris/HCl pH 7.4 @ 25° C., 12.5 mM $MgCl_2$, 1 mM EDTA, 0.2% BSA). Saturation binding studies for determination of $K_d$ values of the radioligand were done using [$^3$H]dihydroalprenolol (NET-720, 100 Ci/mmol, PerkinElmer Life Sciences Inc., Boston, Mass.) at 10 different concentrations ranging from 0.01 nM–200 nM. Displacement assays for determination of $pK_i$ values of compounds were done with [$^3$H]dihydroalprenolol at 1 nM and 10 different concentrations of compound ranging from 40 pM–10 μM. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer. Non-specific binding was determined in the presence of 10 μM unlabeled alprenolol. Assays were incubated for 90 minutes at room temperature, binding reactions were terminated by rapid filtration over GF/B glass fiber filter plates (Packard BioScience Co., Meriden, Conn.) presoaked in 0.3% polyethyleneimine. Filter plates were washed three times with filtration buffer (75 mM Tris/HCl pH 7.4 @ 4° C., 12.5 mM $MgCl_2$, 1 mM EDTA) to remove unbound radioactivity. Plates were dried, 50 μL Microscint-20 liquid scintillation fluid (Packard BioScience Co., Meriden, Conn.) was added and plates were counted in a Packard Topcount liquid scintillation counter (Packard BioScience Co., Meriden, Conn.). Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 μM alprenolol. $K_i$ values for compounds were calculated from observed $IC_{50}$ values and the $K_d$ value of the radioligand using the Cheng-Prusoff equation (Cheng Y, and Prusoff W H., *Biochemical Pharmacology*, 1973, 22, 23, 3099–108). The receptor subtype selectivity was calculated as the ratio of $K_i(β_1)/K_i(β_2)$. With the exception of Compounds 7, 12, and 17 the compounds tested demonstrated a selectivity of greater than about 10. Thus, a preferred group of compounds are compounds of formula (I) other than Compounds 7, 12 and 17, which demonstrate a selectivity of at least 10 in Test A.

Test B

Whole-cell cAMP Flashplate Assay With a Cell Line Heterologously Expressing Human $β_2$ Adrenergic Receptor For the determination of agonist potencies, a HEK-293 cell line stably expressing cloned human β2 adrenergic receptor (clone H24.14) was grown to confluency in medium consisting of DMEM supplemented with 10% FBS and 500 μg/mL Geneticin. The day before the assay, antibiotics were removed from the growth-medium.

cAMP assays were performed in a radioimmunoassay format using the Flashplate Adenylyl Cyclase Activation Assay System with $^{125}$I-cAMP (NEN SMP004, PerkinElmer Life Sciences Inc., Boston, Mass.), according to the manufacturers instructions.

On the day of the assay, cells were rinsed once with PBS, lifted with Versene 1:5,000 (0.2 g/L EDTA in PBS) and counted. Cells were pelleted by centrifugation at 1,000 rpm and resuspended in stimulation buffer prewarmed to 37° C. at a final concentration of 800,000 cells/mL. Cells were used at a final concentration of 40,000 cells/well in the assay. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer (75 mM Tris/HCl pH 7.4 @ 25° C., 12.5 mM $MgCl_2$, 1 mM EDTA, 0.2% BSA). Compounds were tested in the assay at 10 different concentrations, ranging from 2.5 μM to 9.5 pM. Reactions were incubated for 10 min at 37° C. and stopped by addition of 100 μl ice-cold detection buffer. Plates were sealed, incubated over night at 4° C. and counted the next morning in a topcount scintillation counter (Packard Bio-Science Co., Meriden, Conn.). The amount of cAMP produced per mL of reaction was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the 4-parameter model for sigmoidal dose-response with variable slope. Agonist potencies were expressed as $pEC_{50}$ values. All of the compounds tested demonstrated $pEC_{50}$ values greater than about 7. Preferred compounds of formula (I) demonstrate $pEC_{50}$ values greater than about 8 in Test B. More preferred compounds of formula (I) are compounds that demonstrate $pEC_{50}$ values greater than about 9.2 in Test B.

The following synthetic examples are offered to illustrate the invention, and are not to be construed in any way as limiting the scope of the invention.

EXAMPLES

In the examples below, the following abbreviations have the following meanings. Any abbreviations not defined have their generally accepted meaning. Unless otherwise stated, all temperatures are in degrees Celsius.

| | |
|---|---|
| DMSO = | dimethyl sulfoxide |
| EtOAc = | ethyl acetate |
| TFA = | trifluoroacetic acid |
| THF = | tetrahydrofuran |
| MgSO$_4$ = | anhydrous magnesium sulfate |
| NaHMDS = | sodium hexamethyldisilazane |
| TMSCl = | trimethylsilyl chloride |
| DMF = | dimethyl formamide |

General: Unless noted otherwise, reagents, starting material and solvents were purchased from commercial suppliers, for example Sigma-Aldrich (St. Louis, Mo.), J. T. Baker (Phillipsburg, N.J.), and Honeywell Burdick and Jackson (Muskegon, Mich.), and used without further purification; reactions were run under nitrogen atmosphere; reaction mixtures were monitored by thin layer chromatography (silica TLC), analytical high performance liquid chromatography (anal. HPLC), or mass spectrometry; reaction mixtures were commonly purified by flash column chromatography on silica gel, or by preparative HPLC using the general protocol described below; NMR samples were dissolved in deuterated solvent (CD$_3$OD, CDCl$_3$, or DMSO-d6), and spectra were acquired with a Varian Gemini 2000 instrument (300 MHz) under standard parameters; and mass spectrometric identification was performed by an electrospray ionization method (ESMS) with a Perkin Elmer instrument (PE SCIEX API 150 EX).

Example 1

Synthesis of Compound 1

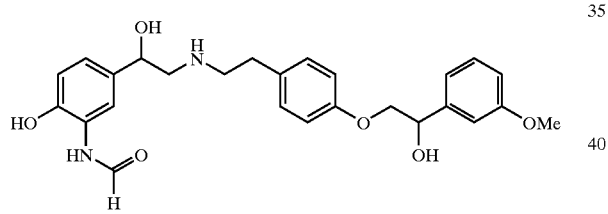

To 50 mg (0.1 mmol) of compound h in 1.5 mL of acetonitrile was added 97 mg (0.3 mmol) of CsCO$_3$. After 5 minutes of vigorous stirring at 80° C., 45 mg (0.2 mmol) of 3-methoxyphenacyl bromide was added. After another 12 h at 45° C., 100 µL of methanol and 12 mg (0.3 mmol) of NaBH$_4$ were added at 0° C. After 30 min at RT, 10 mg of ammonium chloride was added, and the reaction stirred vigorously. After 2 hours, the suspension was filtered, and concentrated in vacuo to a light brown oil. The oil was dissolved in 1 mL methanol, and charged with 5 mg of 10% palladium on charcoal, and placed under hydrogen atmosphere. After a final 12 hours, the suspension was diluted to a total volume of 2 mL with DMF, filtered, and purified by reversed phase HPLC, using a mass-triggered, automated collection device. The product containing fractions were analyzed by analytical LC-MS, and freeze-dried to give compound 1 as a white powder. (10.2 mg; 22%). Retention time (anal. HPLC: Bonus-RP C18, 3.5 µm, 2.1×50 mm, A: 90% ACN; B: 0.1% TFA; 0 min 10% B; 5 min 70%B, 0.5 mL/min, UV @ 214 nm): 2.79 min. m/z calcd for C$_{31}$H$_{32}$N$_2$O$_4$ (M+H$^+$), 467.5, found 467.2.

Intermediate compound h was prepared as follows.

a. Synthesis of Compound f.

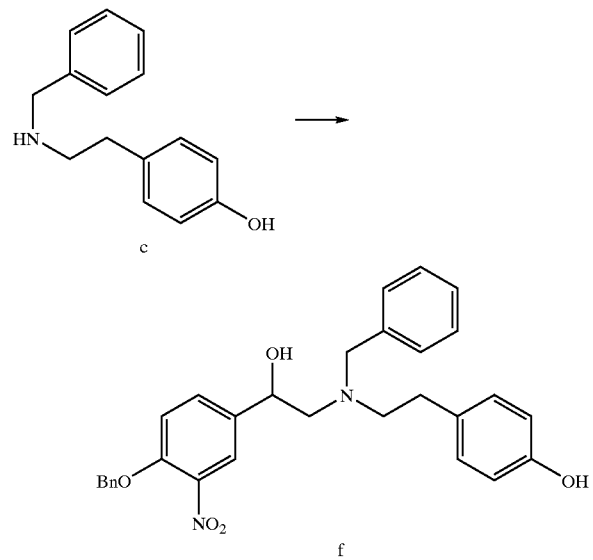

To 1 g (4.4 mmol) of compound c in 10 mL of DMF was added 5 g (60 mmol) of NaHCO$_3$ and 3.1 g (8.8 mmol) of 4-benzyloxy-3-nitrophenacyl bromide. After 12 h at room temperature, 10 mL of THF, 1 mL of methanol and NaBH$_4$ 4 g (109 mmol) were added at 0° C. After stirring for 1 h at room temperature, 300 mL of aqueous ammonium chloride was slowly added. Finally, the mixture was extracted with CH$_2$Cl$_2$, washed with brine, dried over Na$_2$SO$_4$, filtered and concentrated in vacuo to give compound f as an oil.

The intermediate compound c can be prepared as described in Example 6, part c.

b. Synthesis of Compound g.

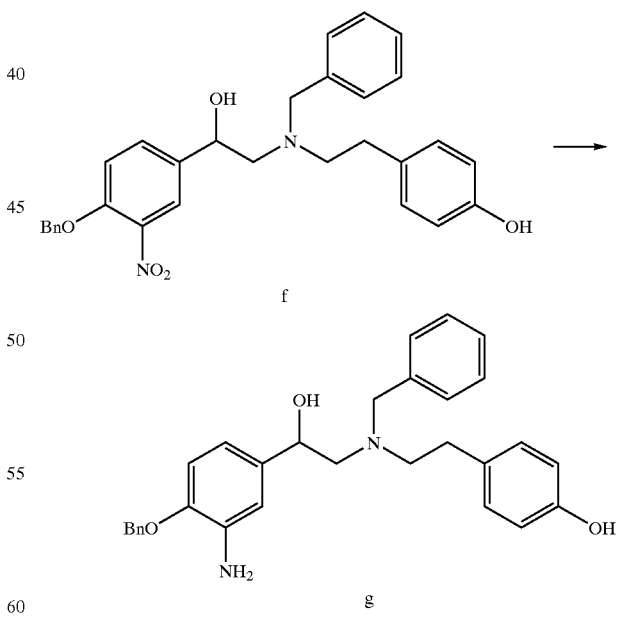

To 2.5 g, (5.2 mmol) compound f in 50 mL of DMF was added SnCl$_2$ (3.38 g, 15 mmol). After 5 h at room temperature, 418 µL (5.2 mmol) of conc. HCl was added. After 1 h at room temperature, 4.2 g of NaHCO$_3$ was added to the reaction and stirred for 2 h then filtered and concentrated in vacuo. The oil was purified by silica gel chromatography (600 mL silica gel, eluted with hexane/EtOAc: 1:1–1:3) to give compound g as an oil. (1.83 g, 62%)

c. Synthesis of Compound h.

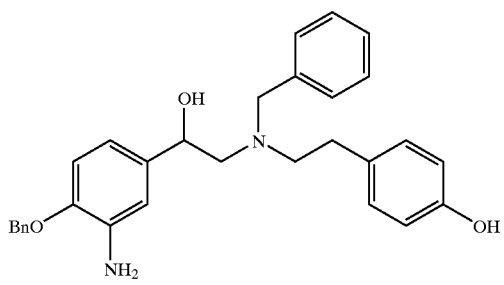

g

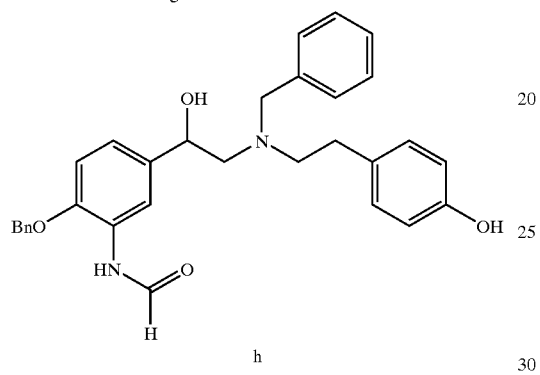

h

To 1.84 g (3.93 mmol) of compound g in CHCl$_3$ at 0° C. was added a mixture containing 241 μL of formic acid and 780 μL of acetic anhydride. After 20 min at room temperature, the mixture was neutralized with saturated NaHCO$_3$, extracted with ethyl acetate, washed with brine, dried over Na$_2$SO$_4$, filtered and concentrated in vacuo. The oil was purified by silica gel chromatography (600 mL silica gel, eluted with hexane/EtOAc: 1:1–1:3) to give compound h as an oil. (1.3 g, 65%). $^1$H NMR (DMSO-d$_6$, 300 MHz): δ2.45–2.9 (m, 4H, CH$_2$H$_2$), δ3.7 (s, 2H, NCH$_2$Ph), δ3.55 and δ3.85 (2d, 2H, CH$_2$), δ4.6 (dd, 1H, CHOH), δ5.05 (s, 2H, OCH$_2$Ph), δ6.75 (d, 2H, Ar), δ6.95 (d, 2H, Ar), δ7.2–7.45 (m, 13H, Ar), δ7.95 (s, 1H).

Example 2

Synthesis of Compound 2

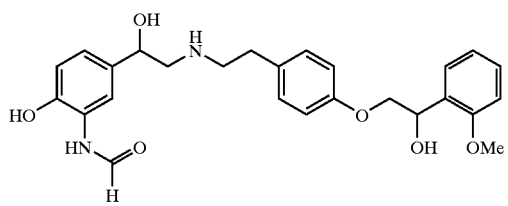

Using a coupling procedure similar to that described in Example 1, except replacing 3-methoxyphenacyl bromide with 2-methoxyphenacyl bromide, compound 2 was prepared. m/z calcd for C$_{26}$H$_{30}$N$_2$O$_5$ (M+H$^+$), 467.5, found 467.2.

Example 3

Synthesis of Compound 3

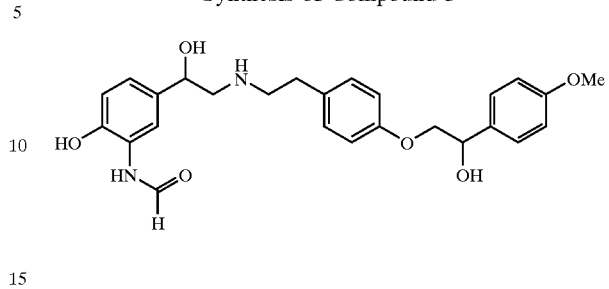

Using a coupling procedure similar to that described in Example 1, except replacing the 3-methoxyphenacyl bromide with 4-methoxyphenacyl bromide, compound 3 was prepared. m/z calcd for C$_{26}$H$_{30}$N$_2$O$_5$ (M+H$^+$), 467.5, found 467.2.

Example 4

Synthesis of Compound 4

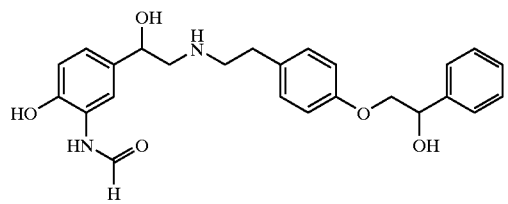

Using a coupling procedure similar to that described in Example 1, except replacing 3-methoxyphenacyl bromide with bromo acetophenone, compound 4 was prepared. m/z calcd for C$_{25}$H$_{28}$N$_2$O$_5$ (M+H$^+$), 437.5, found 437.2.

Example 5

Synthesis of Compound 5

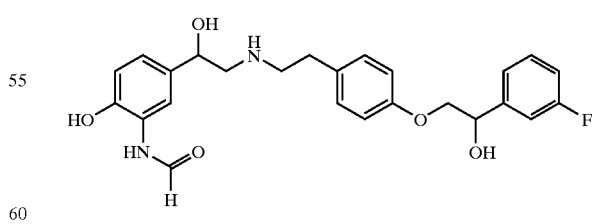

Using a coupling procedure similar to that described in Example 1, except replacing 3-methoxyphenacyl bromide with 3-fluorophenacyl bromide, compound 5 was prepared. m/z calcd for C$_{26}$H$_{30}$N$_2$O$_5$ (M+H$^+$), 455.5, found 455.0.

Example 6

Synthesis of Compound 6

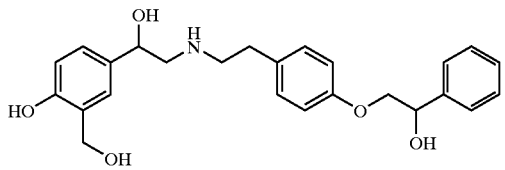

Using a coupling procedure similar to that described in Example 1, except replacing compound h with compound e and 3-methoxyphenacyl bromide with bromo acetophenone, compound 6 was prepared. m/z calcd for $C_{25}H_{29}NO_5$ (M+H$^+$), 424.5, found 424.0.

The intermediate compound e was prepared as follows.

a. Synthesis of Compound a.

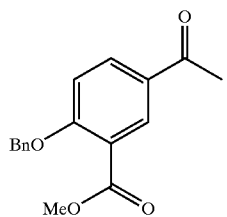

To methyl 5-acetylsalicylate 25 g (0.128 mol) and 50 g (0.38 mol) of $K_2CO_3$ in 250 mL of acetonitrile, was added 17.4 mL (0.140 mol) of benzylbromide. After stirring for 24 hours, the mixture was cooled to room temperature, filtered, the residue was extracted with ethyl acetate, washed with brine, dried over $Na_2SO_4$, filtered and concentrated in vacuo to give a white solid without further purification. (35.18 g, 96.6%). $^1$H NMR (CDCl$_3$, 300 MHz): δ2.6 (s, 3H, COCH$_3$), δ3.95 (s, 3H, COOCH$_3$), δ5.25 (s, 3H, OCHPh), δ7.05 (d, 1H, Ar), δ7.2–7.4 (m, 5H, Ar), δ8.05 (d, 1H, Ar), δ8.45 (s, 1H, Ar).

b. Synthesis of Compound b.

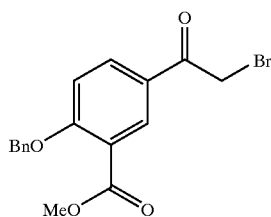

To 10 g (35 mmol) of compound a in 250 mL of chloroform, was added a solution of bromine 1.7 mL (35 mmol) in 50 mL of chloroform. After 3 hours, the reaction was concentrated in vacuo to give a brownish solid. The solid was dissolved in a minimum volume of toluene, diluted with diethyl ether, and the product crystallized to give compound a as a white solid (8.9 g; 70%). $^1$H NMR (CDCl$_3$, 300 MHz): δ3.95 (s, 3H, COOCH$_3$), δ4.4 (s, 3H, CH$_2$Br), δ5.25 (s, 3H, OCHPh), δ7.05 (d, 1H, Ar), δ7.2–7.4 (m, 5H, Ar), δ8.05 (d, 1H, Ar), δ8.45 (s, 1H, Ar).

c. Synthesis of Compound c.

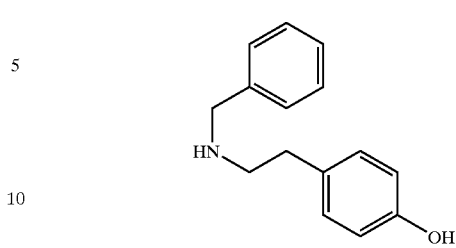

To tyramine (5 g, 36.5 mmol) and benzaldehyde in DMF (10 mL), was added toluene (20 mL). The solution was concentrated to dryness. The concentrate was re-dissolved in methanol (1 mL) and THF (10 mL), and NaBH$_4$ (4 g; 109 mmol) was added in portion at 0° C. After stirring for 1 hours at room temperature, 100 mL of aqueous ammonium chloride was slowly added. Finally, the mixture was extracted with dichloromethane, washed with brine, dried over $Na_2SO_4$, filtered and concentrated in vacuo to give a solid without further purification. (8 g, quant.).

d. Synthesis of Compound d.

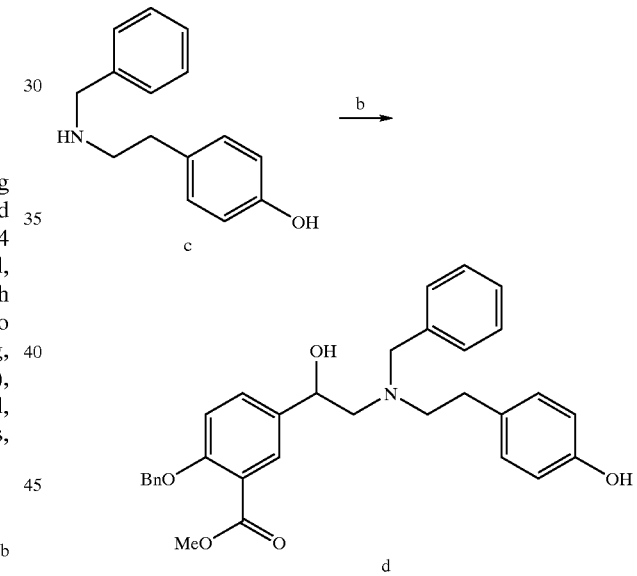

To 8 g (35 mmol) of compound c in 10 mL of DMF was added 9 g (109 mmol) of NaHCO$_3$ and 13 g (36 mmol) of compound b. After 12 h, 10 mL of THF, 1 mL of methanol and 4 g (109 mmol) NaBH$_4$ were added at 0° C. After stirring for 1 hour at room temperature, 300 mL of aqueous ammonium chloride was slowly added. Finally, the mixture was extracted with dichloromethane, washed with brine, dried over $Na_2SO_4$, filtered and concentrated in vacuo. The oil was purified by silica gel chromatography (1000 mL silica gel, eluted with hexane/ethyl acetate: 1:1–1:3) to give compound d as an oil. (15.2 g, 85%) $^1$H NMR (DMSO-d$_6$, 300 MHz): δ2.45–2.9 (m, 4H, CH$_2$H$_2$), δ3.6 (s, 2H, NCH$_2$Ph), δ3.6 and δ3.8 (2d, 2H, CH$_2$), δ3.8 (s, 3H, COOCH$_3$), δ4.6 (m, 1H, CHOH), δ5.25 (s, 2H, OCH$_2$Ph), δ6.6 (d, 2H, Ar), δ6.85 (d, 2H, Ar), δ7.2–7.6 (m, 13H, Ar). m/z calcd for $C_{32}H_{33}NO_5$ (M+H$^+$), 512.6, found 512.2.

e. Synthesis of Compound e.

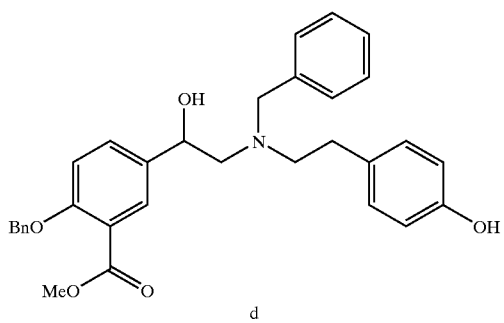

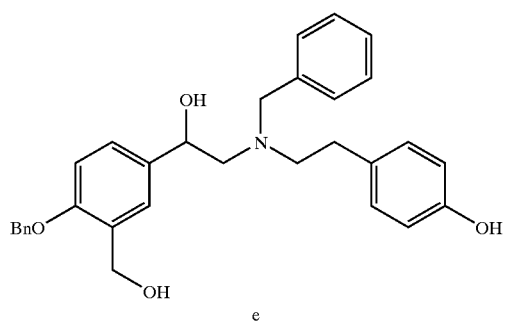

To 15.2 g (31.4 mmol) of compound d in 5 mL of THF, was added 35 mL (35 mmol) of 1M lithium aluminum hydride in tetrahydrofuran. After 30 minutes at 85° C., 20 g of sodium sulfate decahydrate was added in portions. The suspension was filtered and concentrated in vacuo to give compound e as a light yellow oil. (14.36 g, 85%) $^1$H NMR (CDCl$_3$, 300 MHz): δ2.45–2.9 (m, 4H, CH$_2$H$_2$), δ3.4 (s, 2H, NCH$_2$Ph), δ3.6 and δ3.9 (2d, 2H, CH$_2$), δ4.6 (m, 1H, CHOH), δ4.7 (s, 2H, PhCH$_2$OH), δ5.1 (s, 2H, OCH$_2$Ph), δ6.6 (d, 2H, Ar), δ6.9 (d, 2H, Ar), δ7.2–7.6 (m, 13H, Ar).

Example 7

Synthesis of Compound 7

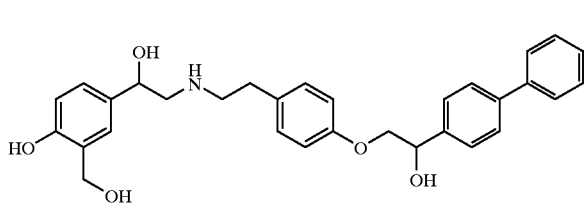

Using a coupling procedure similar to that described in Example 1, except replacing compound h with compound e and 3-methoxyphenacyl bromide with 2-bromo-4'-phenylacetophenone, compound 7 was prepared. m/z calcd for C$_{31}$H$_{33}$NO$_5$ (M+H$^+$), 500.6, found 500.0.

Example 8

Synthesis of Compound 8

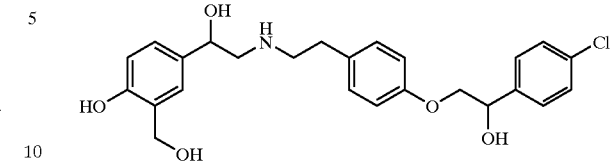

Using a coupling procedure similar to that described in Example 1, except replacing compound h with compound e and 3-methoxyphenacyl bromide with 4-chlorophenacyl bromide, compound 8 was prepared. m/z calcd for C$_{25}$H$_{28}$ClNO$_5$ (M+H$^+$), 458.9, found 558.0.

Example 9

Synthesis of Compound 9

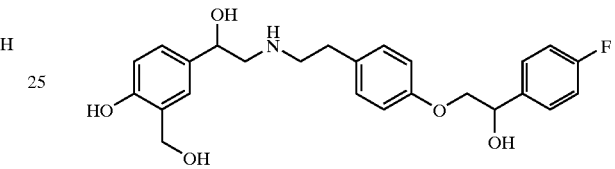

Using a coupling procedure similar to that described in Example 1, except replacing compound h with compound e and 3-methoxyphenacyl bromide with 4-fluorophenacyl bromide, compound 9 was prepared. m/z calcd for C$_{25}$H$_{28}$FNO$_5$ ((M+H$^+$), 442.5, found 442.2.

Example 10

Synthesis of Compound 10

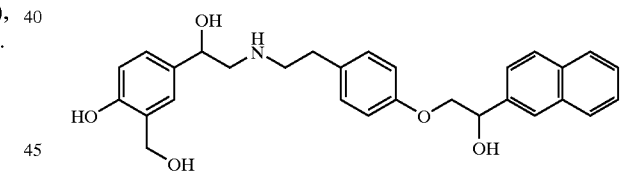

Using a coupling procedure similar to that described in Example 1, except replacing compound h with compound e and 3-methoxyphenacyl bromide with 2-bromo-2'-acetonaphthone, compound 10 was prepared. m/z calcd for C$_{29}$H$_{31}$NO$_5$ (M+H$^+$), 474.6, found 474.1.

Example 11

Synthesis of Compound 11

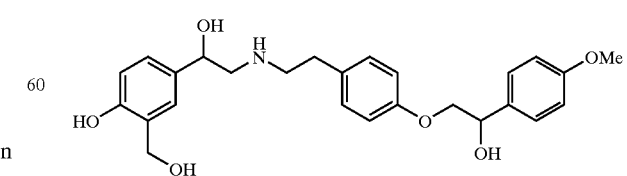

Using a coupling procedure similar to that described in Example 1, except replacing compound h with compound e and 3-methoxyphenacyl bromide with 4-methoxyphenacyl bromide, compound 11 was prepared. m/z calcd for $C_{26}H_{31}NO_6$ (M+H$^+$), 454.5, found 454.2.

Example 12

Synthesis of Compound 12

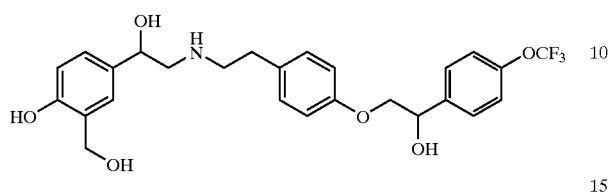

Using a coupling procedure similar to that described in Example 1, except replacing compound h with compound e and 3-methoxyphenacyl bromide with 4-(trifluoromethoxy) phenacyl bromide, compound 12 was prepared. m/z calcd for $C_{26}H_{31}NO_6$ (M+H$^+$), 508.5, found 508.0.

Example 13

Synthesis of Compound 13

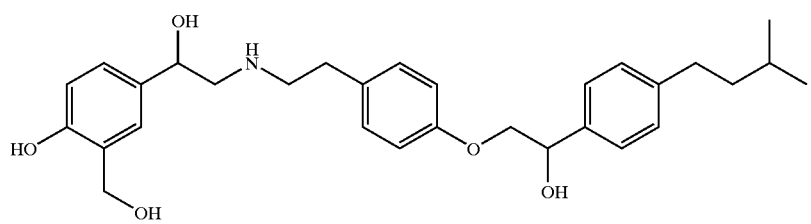

Using a coupling procedure similar to that described in Example 1, except replacing compound h with compound e and 3-methoxyphenacyl bromide with 4-(3-methylbutyl) phenacyl bromide, compound 13 was prepared. m/z calcd for $C_{30}H_{39}NO_5$ (M+H$^+$), 494.6, found 494.2.

Example 14

Synthesis of Compound 14

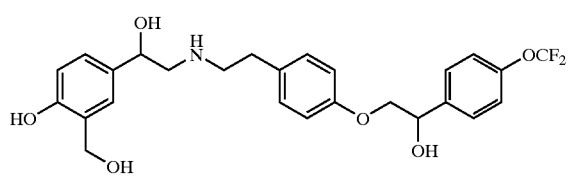

Using a coupling procedure similar to that described in Example 1, except replacing compound h with compound e and 3-methoxyphenacyl bromide with 4-(difluoromethoxy) phenacyl bromide, compound 14 was prepared. m/z calcd for $C_{26}H_{29}FNO_6$ (M+H$^+$), 490.5, found 490.0.

Example 15

Synthesis of Compound 15

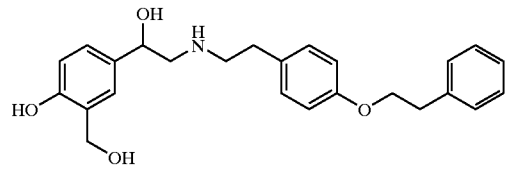

Using a coupling procedure similar to that described in Example 1, except replacing compound h with compound e and 3-methoxyphenacyl bromide with 2-bromoethylbenzene, compound 15 was prepared. m/z calcd for $C_{25}H_{29}NO_4$ (M+H$^+$), 408.5, found 408.0.

Example 16

Synthesis of Compound 16

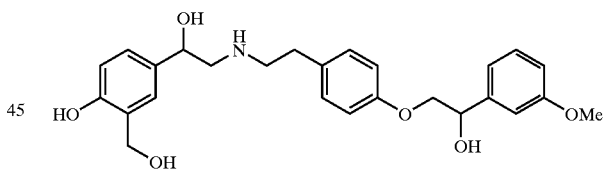

Using a coupling procedure similar to that described in Example 1, except replacing compound h with compound e, compound 16 was prepared. m/z calcd for $C_{25}H_{29}NO_4$ (M+H$^+$), 454.5, found 453.2.

Example 17

Synthesis of Compound 17

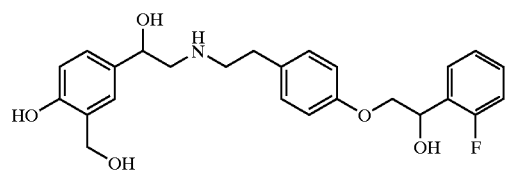

Using a coupling procedure similar to that described in Example 1, except replacing compound h with compound e and 3-methoxyphenacyl bromide with 2-fluorophenacyl bromide, compound 17 was prepared. m/z calcd for $C_{25}H_{28}FNO_5$ (M+H$^+$), 441.5, found 441.2.

Example 18

Synthesis of Compound 18

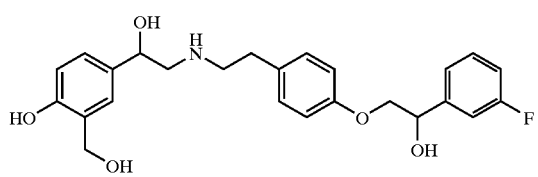

Using a coupling procedure similar to that described in Example 1, except replacing compound h with compound e and 3-methoxyphenacyl bromide with 3-fluorophenacyl bromide, compound 18 was prepared. m/z calcd for $C_{25}H_{28}FNO_5$ (M+H$^+$), 441.5, found 437.0.

Example 19

Synthesis of Compound 19

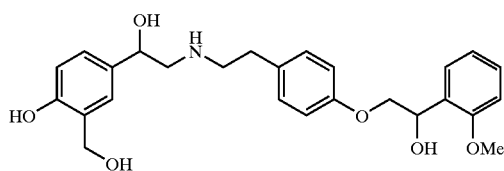

Using a coupling procedure similar to that described in Example 1, except replacing compound h with compound e and 3-methoxyphenacyl bromide with 2-methoxyphenacyl bromide, compound 19 was prepared. m/z calcd for $C_{26}H_{31}NO_6$ (M+H$^+$), 454.5, found 454.3.0.

Example 20

Synthesis of Compound 20

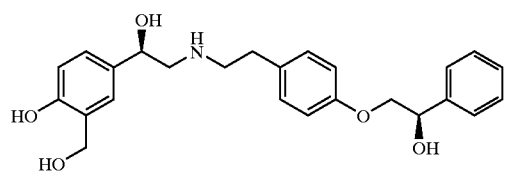

To 821 mg (1.7 mmol) of compound B and 552 mg (4 mmol) of potassium carbonate in 5 mL of toluene at 100° C. was added 200 mg (1.7 mmol) of styrene oxide. After 12 hours, the mixture was cooled to room temperature. The slurry was diluted with 20 mL of methanol, charged with 5 mg of 10% palladium on charcoal, and placed under hydrogen atmosphere. After a final 12 hours, the suspension was filtered, the solution concentrated and the product purified by preparative HPLC (gradient 2–40 acetonitrile in 0.1% TFA). Fractions containing pure product were combined and freeze dried to afford compound 20 as a white powder (47 mg; 6.5%). m/z calcd for $C_{25}H_{29}NO_5$ (M+H$^+$), 424.5, found 424.3.

The intermediate compound A was prepared as follows.

a. Synthesis of Compound A.

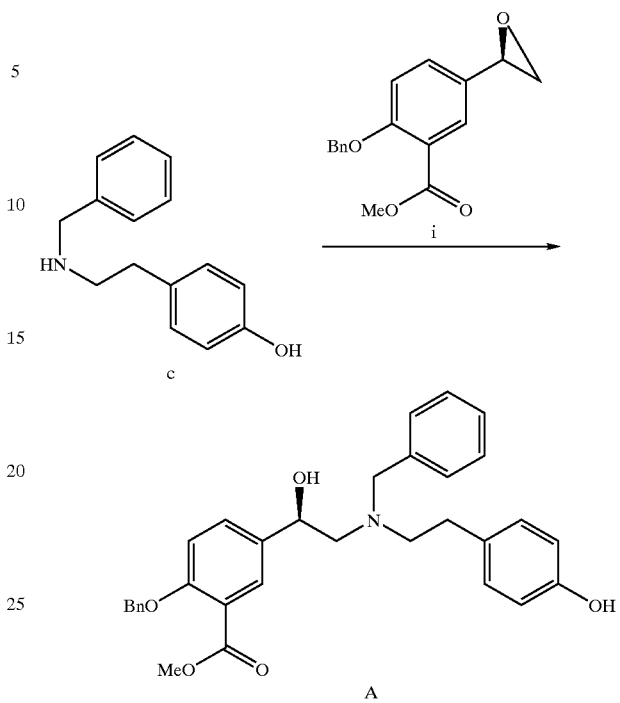

To 1 g (2 mmol) of compound c in 1 mL of toluene at 100° C. was added 568 mg (2 mmol) of epoxide i. After 12 hours, the mixture was cooled to room temperature and purified by silica gel chromatography (100 mL silica gel, eluted with hexane/ethyl acetate: 1:1–1:3) to give compound A as an oil (0.85 g, 95%). m/z calcd for $C_{32}H_{33}NO_5$ (M+H$^+$), 512.6, found 512.5.

b. Synthesis of Compound B.

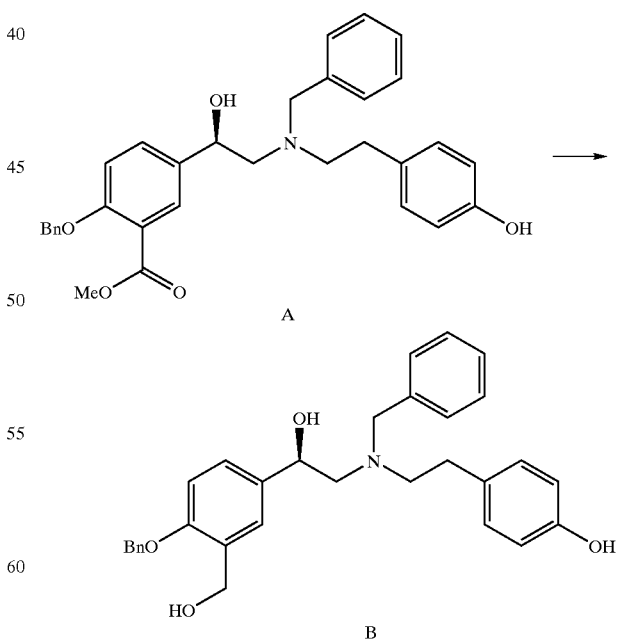

To 850 mg (1.66 mmol) of compound A was added 6 mL (6 mmol) of 1M lithium aluminum hydride in tetrahydrofuran was added. After 30 minutes at 85° C., 10 g of sodium sulfate decahydrate was added in portion. The suspension was filtered and concentrated in vacuo to give compound B as a light yellow oil (821 mg, 85%). m/z calcd for $C_{31}H_{33}NO_4$ (M+H$^+$), 484.6, found 484.3.

The intermediate compound c can be prepared as described in Example 6, part c.

The intermediate epoxide i can be prepared as described by R. Hett et al., *Tetrahedron Lett.*, 1994, 35, 9357–9378.

Example 21

Synthesis of Compound 21

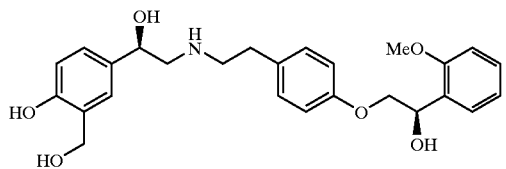

Using a coupling procedure similar to that described in Example 20, except replacing styrene oxide with 2-methoxystyrene oxide, compound 21 was prepared.

Example 22

Synthesis of Compound 22

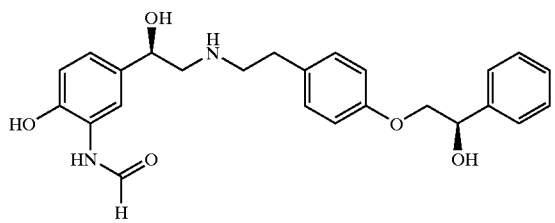

To 882 mg (1.77 mmol) of Compound B and 552 mg (4 mmol) of potassium carbonate in 5 mL of toluene at 100° C. was added 208 mg (1.77 mmol) of styrene oxide. After 12 hours, the mixture was cooled to room temperature. The slurry was diluted with 20 mL of methanol, charged with 5 mg of 10% palladium on charcoal, and placed under hydrogen atmosphere. After a final 12 hours, the suspension was filtered, the solution concentrated and the product purified by preparative HPLC (gradient 2–40 acetonitrile in 0.1% TFA). Fractions containing pure product were combined and freeze dried to afford compound 22 as a white powder. (59 mg; 7.6%) m/z calcd for $C_{25}H_{28}N_2O_5$ (M+H$^+$), 437.5, found 437.3.

The intermediate compound B was prepared as follows.

a. Synthesis of Compound B.

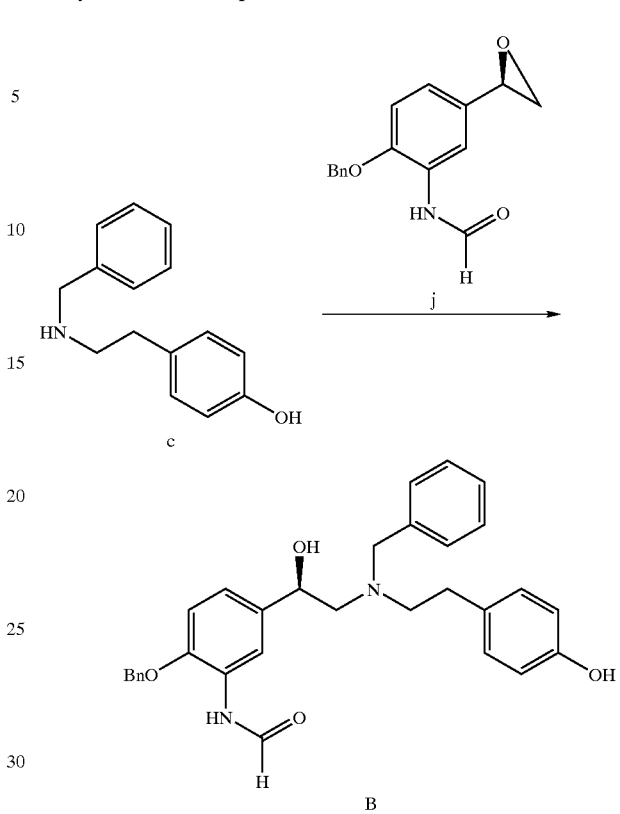

To 1 g (2 mmol) of compound c in 1 mL of toluene at 100° C. was added 538 mg (2 mmol) of epoxide j. After 12 hours, the mixture was cooled to room temperature and concentrated in vacuo to give compound B as a light yellow oil. (882 mg, 89%). m/z calcd for $C_{31}H_{32}N_2O_4$ (M+H$^+$), 497.6, found 497.3.

The intermediate compound c can be prepared as described in Example 6, part c.

The intermediate epoxide j can be prepared as described by Hong et al., *Tetrahedron Lett.*, 1994, 35, 6631.

Example 23

Synthesis of Compound 23

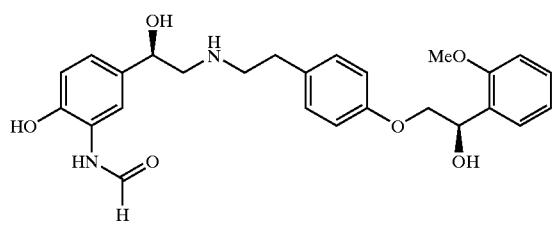

Using a coupling procedure similar to that described in Example 22, except replacing styrene oxide with 2-methoxystyrene oxide, compound 23 was prepared. m/z calcd for $C_{26}H_{30}N_2O_6$ (M+H$^+$), 467.5, found 467.2, 88% ee.

Example 24

Synthesis of Compound 24

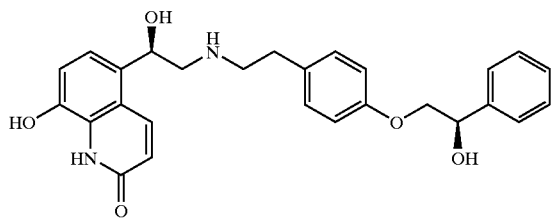

To 915 g (1.76 mmol) of compound C and 552 mg (4 mmol) of potassium carbonate in 5 mL of Toluene at 100° C. was added 208 mg (1.77 mmol) of styrene oxide. After 12 hours, the mixture was cooled to room temperature. The slurry was diluted with 20 mL of methanol, charged with 5 mg of 10% palladium on charcoal, and placed under hydrogen atmosphere. After a final 12 hours, the suspension was filtered, the solution concentrated and the product purified by preparative HPLC (gradient 2–40 acetonitrile in 0.1% TFA). Fractions containing pure product were combined and freeze dried to afford compound 24 as a white powder. (29 mg; 3.1%) m/z calcd for $C_{27}H_{28}N_2O_5$ (M+H$^+$), 461.5, found 461.3.

The intermediate compound C was prepared as follows.
a. Synthesis of Compound C.

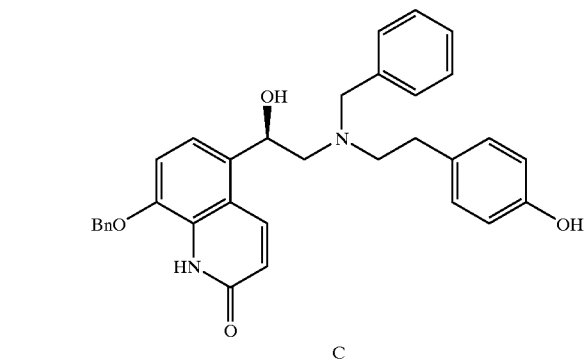

To 1 g (1.9 mmol) of compound c in 1 mL of Toluene at 100° C. was added 556 mg (2 mmol) of epoxide k. After 12 hours, the mixture was cooled to room temperature and concentrated in vacuo to give compound C as a light yellow oil. (915 mg, 88%) m/z calcd for $C_{26}H_{30}N_2O_6$ (M+H$^+$), 521.6, found 521.3.

The intermediate compound c can be prepared as described in Example 6, part c.

The intermediate epoxide k can be prepared as described in International Patent Application Publication Number WO 95/25104; and as described in EP 0 147 719 A2 and EP 0 147 791 B.

Example 25

Synthesis of Compound 25

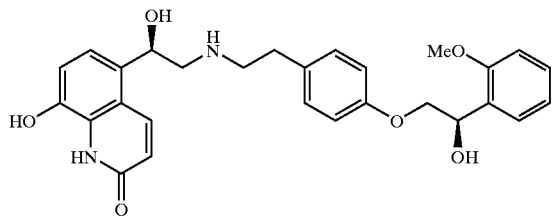

Using a coupling procedure similar to that described in Example 24, except replacing styrene oxide with 2-methoxystyrene oxide, compound 25 was prepared. m/z calcd for $C_{28}H_{30}N_2O_6$ (M+H$^+$), 491.5, found 491.3.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A compound of formula (I):

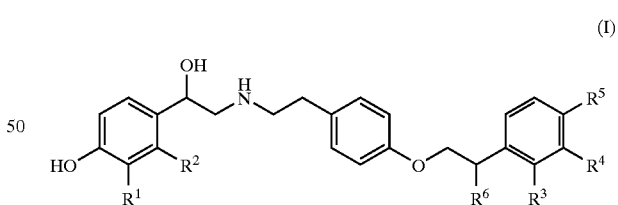

wherein:

$R^1$ is —CH$_2$OH or —NHCHO, and $R^2$ is hydrogen; or $R^1$ and $R^2$ taken together are —NHC(=O)CH=CH—;

$R^3$, $R^4$, and $R^5$ are each independently hydrogen, halo, alkyl, alkoxy, or aryl, wherein each alkyl and alkoxy is optionally substituted with one or more halo; or $R^3$ and $R^4$ together form a fused benzo ring; or $R^4$ and $R^5$ together form a fused benzo ring; and $R^6$ is hydrogen or hydroxy;

or a pharmaceutically-acceptable salt or solvate or stereoisomer thereof.

2. The compound of claim 1 which is a compound of formula (II):

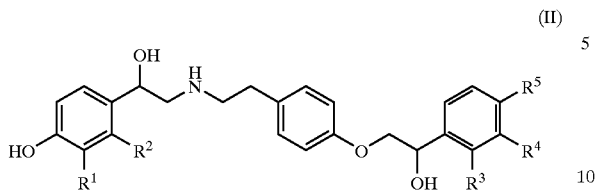

(II)

wherein:
R¹ is —CH₂OH or —NHCHO, and R² is hydrogen; or R¹ and R² taken together are —NHC(=O)CH=CH—; and R³, R⁴, and R⁵ are each independently hydrogen, halo, alkyl, alkoxy, or aryl, wherein each alkyl and alkoxy is optionally substituted with one or more halo; or R³ and R⁴ together form a fused benzo ring; or R⁴ and R⁵ together form a fused benzo ring;

or a pharmaceutically-acceptable salt or solvate or stereoisomer thereof.

3. The compound of claim 1 which is a compound of formula (III):

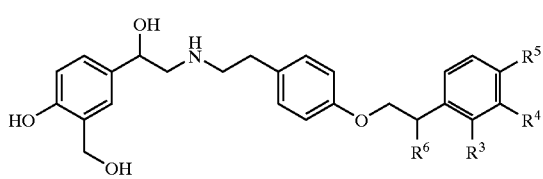

(III)

wherein:
R³, R⁴, and R⁵ are each independently hydrogen, halo, alkyl, alkoxy, or aryl, wherein each alkyl and alkoxy is optionally substituted with one or more halo; or R³ and R⁴ together form a fused benzo ring; or R⁴ and R⁵ together form a fused benzo ring; and R⁶ is hydrogen or hydroxy;

or a pharmaceutically-acceptable salt or solvate or stereoisomer thereof.

4. The compound of claim 1 which is a compound of formula (IV):

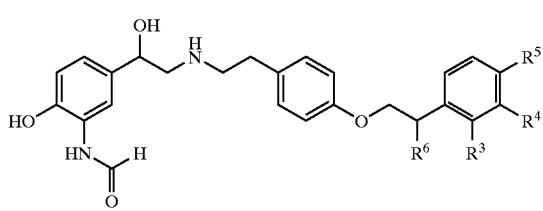

(IV)

wherein:
R³, R⁴, and R⁵ are each independently hydrogen, halo, alkyl, alkoxy, or aryl, wherein each alkyl and alkoxy is optionally substituted with one or more halo; or R³ and R⁴ together form a fused benzo ring; or R⁴ and R⁵ together form a fused benzo ring; and R⁶ is hydrogen or hydroxy;

or a pharmaceutically-acceptable salt or solvate or stereoisomer thereof.

5. The compound of claim 1 which is a compound of formula (V):

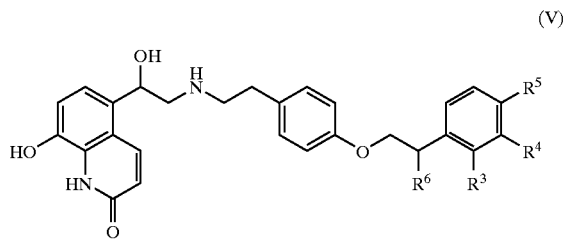

(V)

wherein:
R³, R⁴, and R⁵ are each independently hydrogen, halo, alkyl, alkoxy, or aryl, wherein each alkyl and alkoxy is optionally substituted with one or more halo; or R³ and R⁴ together form a fused benzo ring; or R⁴ and R⁵ together form a fused benzo ring; and R⁶ is hydrogen or hydroxy;

or a pharmaceutically-acceptable salt or solvate or stereoisomer thereof.

6. The compound of claim 2 wherein R³ is hydrogen, alkoxy or halo.

7. The compound of claim 2 wherein R⁴ is hydrogen, alkoxy or halo.

8. The compound of claim 2 wherein R⁴ and R⁵ together from a fused benzo ring.

9. The compound of claim 2 wherein R⁵ is hydrogen, alkyl, aryl, alkoxy or halo.

10. The compound of claim 2 wherein R⁵ is hydrogen, fluoro, chloro, methoxy, trifluoromethoxy, difluoromethoxy, 3-methylbutyl, or phenyl.

11. The compound of claim 2 wherein R³ is hydrogen or methoxy; R⁴ is hydrogen or methoxy; and R⁵ is hydrogen.

12. The compound of claim 2 wherein R³ is hydrogen; R⁴ is hydrogen; and R⁵ is hydrogen.

13. The compound of claim 1 wherein R⁶ is hydroxy, which is the (R, R) diastereomer at the chiral center attached to the phenyl ring substituted with R¹ and R² and at the chiral center substituted with R⁶ in formula (I).

14. The compound of claim 2, which is the (R, R) diastereomer at the chiral center attached to the phenyl ring substituted with R¹ and R² and at the chiral center attached to the phenyl ring substituted with R³, R⁴, and R⁵ in formula (II).

15. The compound of claim 1 which is any one of compounds 1–25; or a pharmaceutically-acceptable salt or solvate or stereoisomer thereof.

16. A compound selected from the group consisting of:

4-((R)-1-Hydroxy-2-{2-[4-((R)-2-hydroxy-2-phenyl-ethoxy)-phenyl]-ethylamino}-ethyl)-2-hydroxymethyl-phenol;

4-[(R)-1-Hydroxy-2-(2-{4-[(R)-2-hydroxy-2-(2-methoxy-phenyl)-ethoxy]-phenyl}-ethylamino)-ethyl]-2-hydroxymethyl-phenol;

N-[2-Hydroxy-5-((R)-1-hydroxy-2-{2-[4-((R)-2-hydroxy-2-phenyl-ethoxy)-phenyl]-ethylamino}-ethyl)-phenyl]-formamide;

N-{2-Hydroxy-5-[(R)-1-hydroxy-2-(2-{4-[(R)-2-hydroxy-2-(2-methoxy-phenyl)-ethoxy]-phenyl}-ethylamino)-ethyl]phenyl}-formamide;

8-Hydroxy-5-((R)-1-hydroxy-2-{2-[4-((R)-2-hydroxy-2-phenyl-ethoxy)-phenyl]-ethylamino}-ethyl)-1H-quinolin-2-one;

8-Hydroxy-5-[(R)-1-hydroxy-2-(2-{4-[(R)-2-hydroxy-2-(2-methoxy-phenyl)-ethoxy]-phenyl}-ethylamino)-ethyl]-1H-quinolin-2-one; and pharmaceutically-acceptable salts and solvates and stereoisomers thereof.

17. A pharmaceutical composition comprising a therapeutically effective amount of the compound of claim 1 and a pharmaceutically acceptable carrier.

18. The pharmaceutical composition of claim 17, wherein the composition further comprises a therapeutically effective amount of one or more other therapeutic agents.

19. The pharmaceutical composition of claim 17, wherein the composition is formulated for administration by inhalation.

20. A combination comprising the compound of claim 1 and one or more other therapeutic agents.

21. The combination of claim 20 wherein the other therapeutic agent is a corticosteroid, an antichlolinergic agent, or a PDE4 inhibitor.

22. A combination comprising a compound of claim 1 and a compound selected from the group consisting of fluticasone propionate, 6α,9α-difluoro-17α-[-(2-furanylcarbonyl)oxy]-11β-hydroxy-16α-methyl-3-oxo-androsta-1,4-diene-17β-carbothioic acid S-fluoromethyl ester, and 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester.

23. A method of treating a disease or condition in a mammal associated with $\beta_2$ adrenergic receptor activity, the method comprising administering to the mammal, a therapeutically effective amount of a pharmaceutical composition of claim 17.

24. The method of claim 23 wherein the disease or condition is a pulmonary disease.

25. The method of claim 24 wherein the pulmonary disease is asthma or chronic obstructive pulmonary disease.

26. The method of claim 23 wherein the disease or condition is selected from the group consisting of pre-term labor, neurological disorders, cardiac disorders, and inflammation.

27. The method of claim 23 further comprising administering a therapeutically effective amount of one or more other therapeutic agents.

28. The method of claim 27 wherein the other therapeutic agent is a corticosteroid, an anticholinergic agent, or a PDE4 inhibitor.

29. A method of treating a disease or condition in a mammal associated with $\beta_2$ adrenergic receptor activity, the method comprising administering to the mammal, a therapeutically effective amount of a pharmaceutical composition of claim 18.

30. A method of modulating the activity of a $\beta_2$ adrenergic receptor, the method comprising stimulating a $\beta_2$ adrenergic receptor with a modulatory amount of a compound as described in claim 1.

* * * * *